(12) United States Patent
Duplessie et al.

(10) Patent No.: US 7,022,111 B2
(45) Date of Patent: *Apr. 4, 2006

(54) INTRAVENOUS STABILIZING DEVICE (76) Inventors: Renee F. Duplessie, 7211 Angela, Glendale, AZ (US) 85308; David S. Miller, 7211 Angela, Glendale, AZ (US) 85308

( * ) Notice: Subject to any disclaimer, the term of this patent is extended or adjusted under 35 U.S.C. 154(b) by 341 days.

This patent is subject to a terminal disclaimer.

(21) Appl. No.: 10/117,813

(22) Filed: Apr. 8, 2002

(65) Prior Publication Data

US 2002/0128605 A1 Sep. 12, 2002

Related U.S. Application Data (63) Continuation-in-part of application No. 09/169,251, filed on Oct. 9, 1998, now Pat. No. 6,375,639.

(51) Int. Cl.
*A61M 5/32* (2006.01)
*A61F 15/00* (2006.01)

(52) U.S. Cl. ............... 604/174; 602/42; 128/DIG. 26
(58) Field of Classification Search ............ 604/174, 604/175, 177–180, 305, 307, 308, 351, 352, 604/327, 337, 345; 602/54, 56–8, 42, 60; 606/213–216; 128/DIG. 26, 898–99
See application file for complete search history.

(56) References Cited

U.S. PATENT DOCUMENTS

| | | |
|---|---|---|
| 3,990,454 A | 11/1976 | Schlesinger |
| 4,316,461 A | 2/1982 | Marais et al. |
| 4,445,894 A | 5/1984 | Kovacs |
| 4,449,975 A | 5/1984 | Perry |
| 4,490,141 A | 12/1984 | Lacko et al. |
| 4,591,356 A | 5/1986 | Christie |
| 4,669,458 A | 6/1987 | Abraham et al. |
| 4,737,143 A | 4/1988 | Russell |
| 4,799,923 A | 1/1989 | Campbell |
| 4,941,882 A | 7/1990 | Ward et al. |
| 4,966,590 A | 10/1990 | Kalt |
| 5,188,608 A | 2/1993 | Fritts |
| 5,292,312 A | 3/1994 | Delk et al. |
| 5,306,256 A | 4/1994 | Jose |
| 5,342,317 A | 8/1994 | Claywell |
| 5,372,589 A | 12/1994 | Davis |
| 5,389,092 A | 2/1995 | Guillemet et al. |
| 5,445,604 A | 8/1995 | Lang |
| 5,468,229 A | 11/1995 | Chandler |
| 5,549,567 A | 8/1996 | Wolman |
| 6,124,521 A | 9/2000 | Roberts |
| 6,375,639 B1 * | 4/2002 | Duplessie et al. .......... 604/174 |

* cited by examiner

*Primary Examiner*—Patricia Bianco
(74) *Attorney, Agent, or Firm*—Rader, Fishman & Grauer PLLC (57) ABSTRACT

A stabilizing device for securing an intravenous catheter to a patient's body is described having a main body with a cut out to allow passage of the catheter. The main body includes a front portion connected to a rear portion by a pair of side portions. At least one of the side portions has a slit to enable the cut out to be placed around a previously installed catheter. A plurality of straps are provided to wrap around the affected body portion of a patient. Tabs in various configurations are used to secure catheter tubing to the main body and to prevent unwanted removal of the catheter.

16 Claims, 10 Drawing Sheets

_Fig-1_

_Fig-2_

INTRAVENOUS STABILIZING DEVICE

CROSS REFERENCE TO RELATED APPLICATIONS

The present application is a continuation-in-part of U.S. patent application Ser. No. 09/169,251, filed Oct. 9, 1998 now U.S. Pat. No. 6,375,639. The complete disclosure of U.S. patent application Ser. No. 09/169,251 is hereby incorporated by reference.

FIELD OF THE INVENTION

The present invention relates to a stabilizing device for catheters, and in particular, to intravenous catheters. The stabilizing device of the present invention includes a main body having a cut-out adjacent a needle insertion site and either a plurality of straps to attach the device to a patient's body or being of a wide band encircling the limb or appendage. Smaller narrow portions (loops or tabs) of various configurations are attached to or extend from the main body of the device to secure the IV catheter tubing. The present invention eliminates the need for applying tape directly to the patient's skin.

BACKGROUND OF THE INVENTION

Many of the patients that enter a hospital are given an intravenous (IV) catheter for venous access as well as for the administration of fluids, medications, and parenteral nutrition. In the past, it has been common practice to apply tape directly to securely attach the catheter hub and tubing to the patient. However, certain patients have severe allergy to tape/adhesives. Furthermore, elderly, newborn and burn patients have frail or damaged skin that is not conducive to the use of tape to anchor an IV. In some instances, skin is actually removed when the tape is removed.

Previously, some designs have been proposed to alleviate the problem of direct taping. One such design utilizes a stabilizing sleeve having an outer fabric layer with a gauze inner layer that wraps around a patient's appendage and holds the IV needle and tube against the patient's appendage. The sleeve utilizes VELCRO adjacent a seam to removably fasten the sleeve to the appendage. Disadvantages to this are the potential for a tourniquet effect and the inability to view the area proximal to the IV site, not to mention the difficulty and cost in manufacturing it.

Another previously proposed design utilizes bands that wrap around a patient's appendage adjacent the insertion site of an IV catheter. Ends of the bands attach to each other using a hook and loop fastener system such as Velcro®. Catheter tubing is anchored against the bands by using adhesive tape. Thus, the adhesive tape is applied to the bands and not the patient's skin. Some of the disadvantages to this design include: high cost manufacturing, increased risk of a tourniquet effect, inability to observe the sites proximal and distal to the IV catheter insertion site.

Yet another stabilizer design includes a base unit that is placed against the patient's body and includes wing straps having medical adhesive on one side which wrap around and attach to the base unit to secure the device to the patient. A low profile one-piece tub mount is centrally located in the base unit for grasping a tube.

However, none of the prior art of stabilizing devices have a cut-out to allow viewing of the area adjacent the needle insertion site. In addition, the area proximal to the insertion site is covered, therefore, prohibiting surveillance for IV infiltration. In addition, the prior designs lack the use of a disposable, resilient, surgical grade material that is self-adherent but non-adhesive to a patient's skin or hair. Also, the prior art lacks protection from a tourniquet effect because the materials are non-expansile.

SUMMARY OF THE INVENTION

The present invention is directed to a stabilizing device for securing a catheter having a main body provided with a cut-out window that allows passage of a catheter through it (or through the cut-out portion of the window). The main body further includes a front portion connected to a rear portion by a pair of side portions. At least one of the side portions may have a slit to allow the cut-out to be placed around a previously installed catheter. Straps are connected to the side portions. At least one of the straps extends outwardly away from the main body. These straps are used to attach the main body to a patient's appendage at a catheter needle insertion site. Loops or tabs of various configurations surround the catheter tubing and attach the tubing to the front and rear portions of the main body.

The present invention allows healthcare personnel to view the area adjacent the site of needle insertion to detect signs of complications such as IV catheter infiltration or phlebitis. Another feature of the present invention is the use of non-adhesive, disposable, self-adherent, surgical grade material for the entire device. Thus, the loops or tabs holding the tubing are pressed against the main body to attach the catheter in place. Then the straps can be wrapped around the affected appendage and can be applied over the ends of the loops to further hold the catheter in place. Further, the present invention is made of materials that have inherent extensibility that helps to prevent a tourniquet effect, if moderate swelling of the appendage occurs.

The present invention is directed to an IV stabilizing device which has a wide portion that encircles a limb or appendage with or without smaller narrow portions which secure the IV catheter to the device (not the patient). The wide portion is composed of a single wide band or smaller bands extending from a body (wide portion) to encircle the limb or appendage and connecting via self-adherence. There are many variations possible of this theme, not just the non-adhesive mechanisms illustrated in the figures. Obviously certain designs have advantages over other designs and will be more likely to become commercially used. The device may have the smaller narrow portions (loops or tabs) (which stabilize the IV catheter) either protruding into the central portion of the cut-out window longitudinally, vertically, singularly, or plurally. The device may also have these smaller narrow portions (loops or tabs) protruding away from the body of the device (proximally and distally).

These narrow portions may either be connected to the device or integrally a part of the device. They may also be absent, with adhesive tape being used in their stead, as it will stabilize the IV catheter to the device instead of the patient.

The present invention is cost effective, easy to manufacture, and disposable to insure cleanliness. The present invention can be made of different width materials and therefore can be easily adapted to fit different size bodies and can be applied to different body sites (elbow, forearm, hand, leg, etc.) and is easily applied or removed by healthcare personnel, without the need to remove the IV catheter, by way of the slit opening of the window portion of the body. The device can and will likely be used in combination with a transparent, occlusive type dressing/bandage to maintain sterility of the catheter insertion site for use in patients where minimal adhesive use is not an issue. In patients where it is an issue, a sterile non-stick pad will be used instead.

A larger version can be used for stabilization of a central venous catheter cordis or Swan Ganz catheter by applying the stabilizing device in a figure 8 pattern about the shoulders and axilla, similar to a clavicular fracture splint/bandage.

BRIEF DESCRIPTION OF THE DRAWINGS

The features and inventive aspects of the present invention will become more apparent upon reading the following detailed description, claims, and drawings, of which the following is a brief description:

DETAILED DESCRIPTION OF PREFERRED EMBODIMENTS

Figure 1:
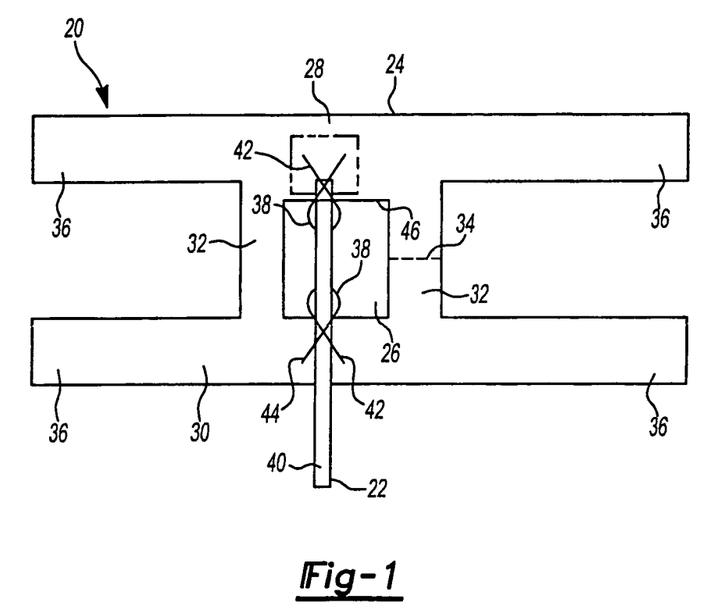
FIG. 1 is top view of a first embodiment of the present invention.

FIG. 1 shows a stabilizing device 20 for securing an intravenous (IV) catheter 22 to a patient's body (not shown). Stabilizing device 20 includes a main body 24 having a window 26 to allow passage of IV catheter 22. Main body 24 further includes a front portion 28 connected to a rear portion 30 by a pair of side portions 32. At least one of the side portions 32 may be provided with a slit 34 to enable window 26 to be placed around the previously installed catheter 22.

A plurality of straps 36 are connected to side portions 32 and extend outwardly away from main body 24. Straps 36 are preferably integral with main body 24 and made of a same extensible surgical grade material. If a non-extensible surgical grade material is to be used, then elastic connections 80 may be incorporated to prevent a tourniquet effect. If another material is used that is not self-adherent, the portions requiring self-adherent qualities may require VELCRO® or adhesive which would increase production costs, thereby making a self-adherent material ideal. One preferred material for stabilizing device 20 is a disposable, self-adherent, surgical grade material supplied by 3M Corporation under the trademark COBAN®. Slight pressure applied to overlapping regions of this material causes the overlapping regions to become fastened together. However, the material does not adhere to hair or skin, eliminating the problems caused by using adhesive tape. COBAN® has some degree of inherent extensibility that reduces the potential for a tourniquet effect if the affected body portion begins to swell. However, any suitable surgical grade material may also be used.

A plurality of loops 38 are attached to, or project internally or externally, from the main body 24 to wrap around and hold tubing 40 of catheter 22. More specifically, one loop 38 is attached to front portion 28 and a second loop 38 is attached to rear portion 30. Loops 38 preferably form a gamma shape or partial figure 8 shape to secure tubing 40 and prevent catheter 22 from being pulled out. Loops 38 can also be made from the same self-adhering surgical grade material as main body 24 and straps 36. Therefore, loops 38 can easily be pressed into place to secure them to main body 24. Additionally, if straps 36 are sufficiently long, they can wrap around the affected region and also overlap ends 42 of loops 38 to further retain loops 38 in position.

As illustrated in FIG. 1, tube 40 rests upon an outer surface 44 of rear portion 30 and contacts an inner surface 46 of front portion 28. Front portion 28 covers the site where a needle (not shown) of catheter 22 is inserted. But, the area adjacent the site of insertion is able to be viewed through window 26 or the area proximal to the IV insertion site by healthcare personnel. Viewing of the adjacent area is important to detect signs of complications, including for example, IV catheter infiltration or phlebitis.

Figure 2:
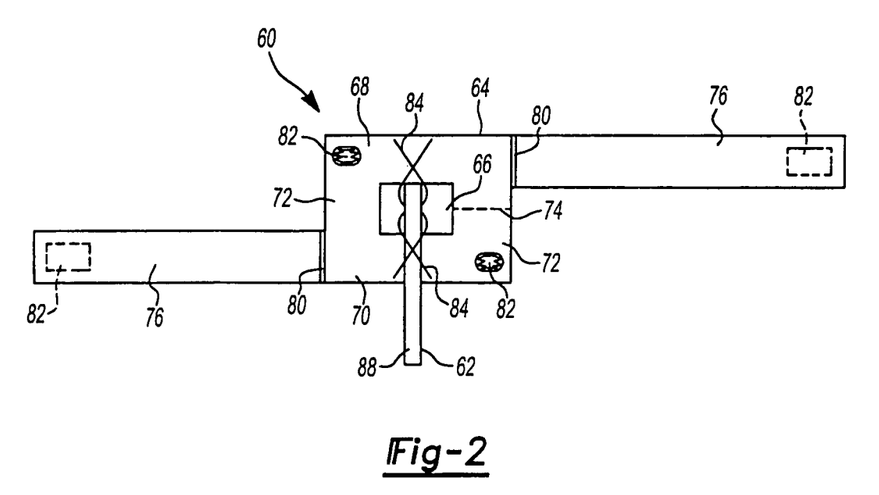
FIG. 2 is a top view of a second embodiment of the present invention.

A second embodiment according to the present invention is shown in FIG. 2. Stabilizing device 60 includes a main body 64 having a window 66 to allow passage of IV catheter 62. Main body 64 further includes a front portion 68 connected to a rear portion 70 by a pair of side portions 72. At least one of the side portions 72 is provided with a slit 74 to enable window 66 to be placed around the previously installed catheter 62.

A plurality of straps 76 are connected to side portions 72 and extend outwardly away from main body 64. Straps 76 are preferably made of a same surgical grade material as main body 64. Straps 76 can be attached to main body 64 using elastic 80 to provide resiliency. In addition, VELCRO® patches 82 can be used to fasten the straps 76 to one another. Loops 84 made of tape can be attached to front and rear portions 68, 70 in a gamma shape or partial figure 8 shape, to retain tubing 88 against main body 64 in a somewhat rigid fashion. However, tape is only applied to the stabilizing device 60, not the skin.

Operation

The operation of the present invention is as follows. First, an IV catheter 22,62 is inserted into a patient's vein and a sterile non-stick pad is applied to the needle insertion site. Next, slit 34, 74 is opened to allow main body 24, 64 to surround tubing 40, 88. After tubing 40, 88 is within window 26, 66, slit 34, 74 is re-closed to prevent unwanted removal of stabilizing device 20, 60. Then, front portion 28, 68 is positioned so as to overlie the sterile pad. Loops 38, 84 are formed into a partial figure eight shape around tubing 40, 88 with the ends of the loops being attached to the respective front and rear portions of main body 24, 64. Next, straps 36, 76 are wrapped around the affected body portion of the patient. As discussed above, the straps 36 are self-adhering and connect to the main body via localized pressure. Straps 76 can be connected using VELCRO®.

Further Embodiments

Figure 3:
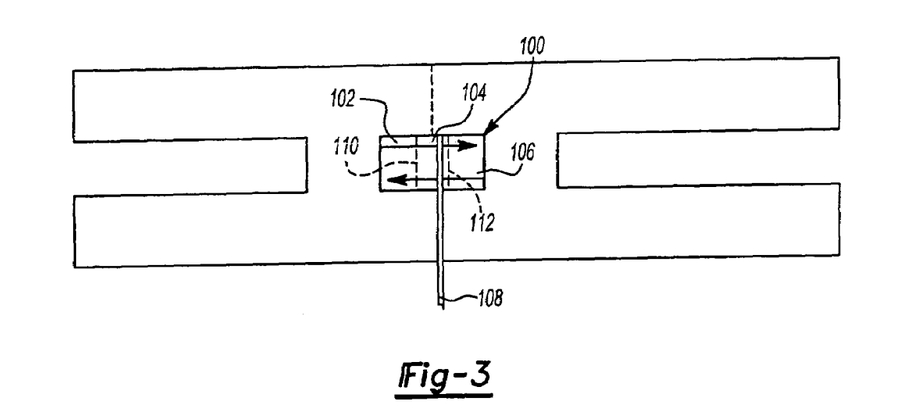
FIG. 3 is a top view of a third embodiment of the present invention.

FIG. 3 shows a third embodiment of the present invention wherein a window 100 is provided with a leftmost panel 102 connected to a middle panel 104 and a rightmost panel 106. Middle panel 104 is stationary and includes a passage to allow a catheter tube 108 to pass from one side of window 100 to the opposite side. Leftmost panel 102 and rightmost panel 106 are connected to middle panel 104 along fold lines 110, 112, and are able to be folded over on top of middle panel 104 to securely stabilize tube 108.

Figure 4:
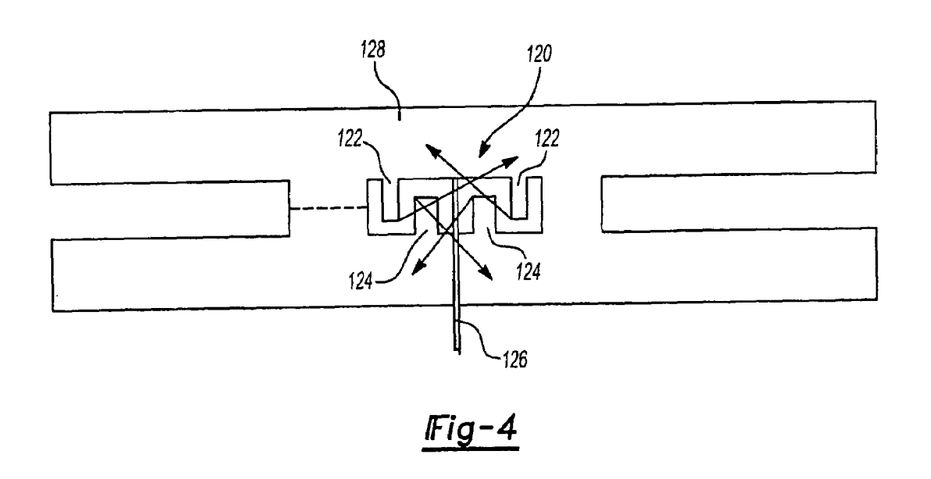
FIG. 4 is a top view of a fourth embodiment of the present invention.

FIG. 4 shows a fourth embodiment of the present invention wherein a window 120 is provided with a pair of upper tabs 122 and a pair of lower tabs 124 that can be integrally formed in window 120. As indicated by the arrows, upper tabs 122 are pulled upwardly and crossed over each other in an "X" pattern underneath tube 126 and then fastened on top of main body 128. Lower tabs 124 are crossed over top of tube 126 as shown by the arrows and fastened to the main body 128 to achieve proper stabilization.

Figure 5:
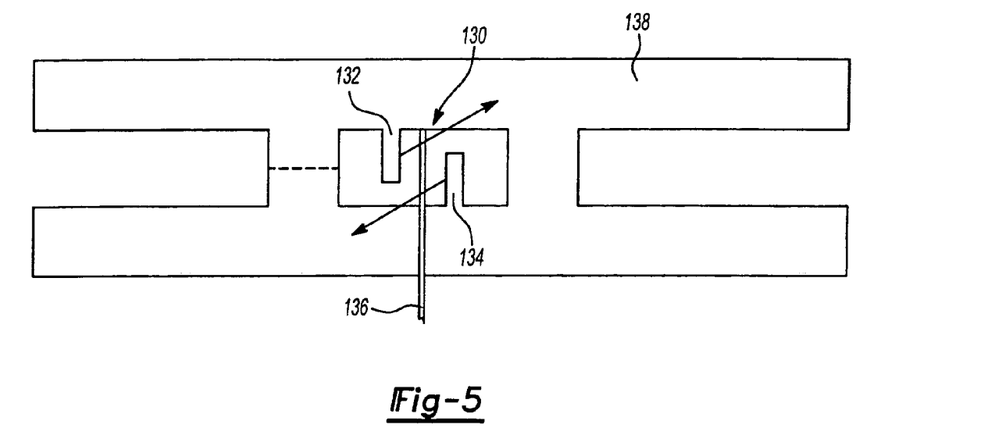
FIG. 5 is a top view of a fifth embodiment of the present invention.

FIG. 5 shows a fifth embodiment wherein a window 130 includes one upper tab 132 and one lower tab 134. Similar to the embodiment of FIG. 4, upper tab 132 travels diagonally under tube 136 and is attached onto main body 138 as indicated by the arrow. Lower tab 134 is folded diagonally back over top of tube 136 and is fastened to main body 138.

Figure 6:
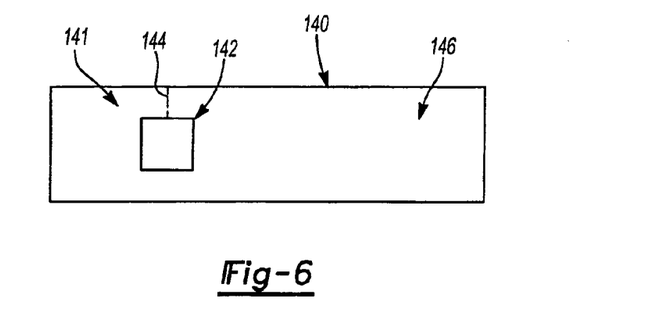
FIG. 6 is a top view of a sixth embodiment of the present invention.
Figure 8:
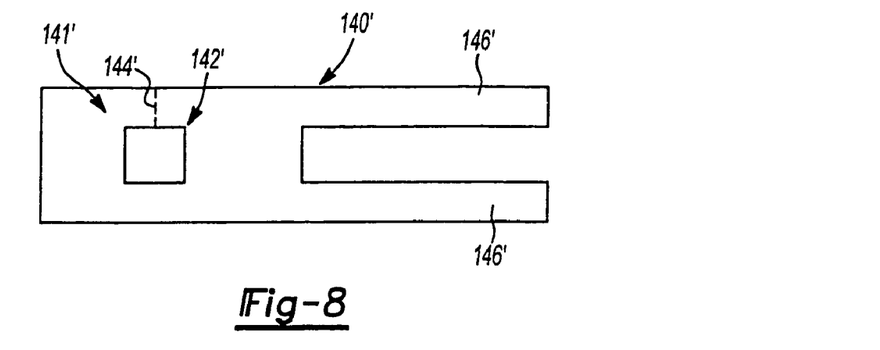
FIG. 8 is a top view of an eighth embodiment of the present invention.

FIG. 6 shows yet another embodiment of the present invention wherein a stabilizing device 140 is made from a single strip of material and has a window 142 and a slit 144 that allows installation around a tube (not shown). The strip can be a self-adherent material or have separate fastening devices attached thereto. The strip includes a strap portion 146 which has sufficient length to encircle a patient's body at the insertion site. Although strap portion 146 is shown as the same width as main body portion 141, it is contemplated that strap portion 146 can be one or more narrow members extending outwardly from main body portion 141 at any location. For example, instead of being a single horizontal member, strap portion 146 can be a pair of vertically spaced apart narrow members 146' that extend horizontally from one side of a main body portion 141'; as shown in FIG. 8. Corresponding elements are labeled as primed numbers.

Figure 7:
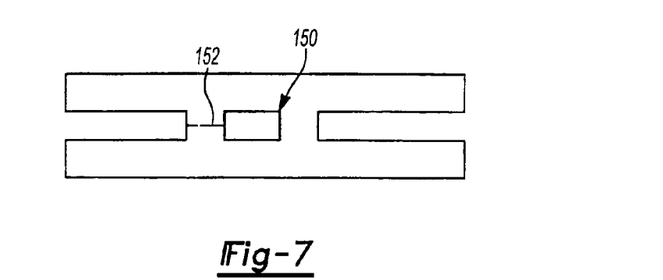
FIG. 7 is a top view of a seventh embodiment of the present invention.

FIG. 7 shows a still further embodiment according to the present invention, wherein a window 150 is provided with a slit 152 and can be used to stabilize a catheter tube without additional loops or tabs.

Figure 9:
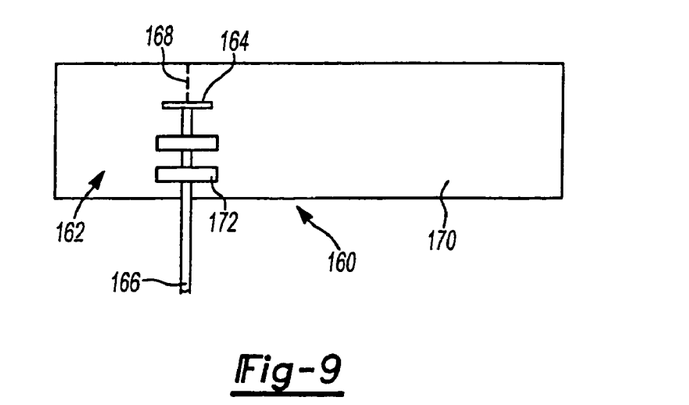
FIG. 9 is a top view of a ninth embodiment of the present invention.

FIG. 9 illustrates another embodiment of the present invention. A stabilizing device 160 is illustrated as being formed as a single strip of material and has a main body portion 162 including an opening 164 having sufficient size for allowing passage of a catheter tube 166. Unlike the previous embodiments, the present opening 164 is not sized to permit viewing an area of the patient's body that is distal to the catheter insertion site. Instead, opening 164 is sized only to permit acceptable passage of a catheter. In fact, opening 164 maybe a single cut in the main body 162. A slit 168 extends to opening 164 from an outer edge of main body portion 162 and allows installation of stabilizing device 160 around a previously installed tube. Slit 168 can be selectively closeable to improve catheter retention. The strip of material can be a self adherent material of have separate fastening devices attached thereto, as described previously. The stabilizing device 160 includes a strap portion 170 which has sufficient length to encircle a patient's body at the insertion site. Although strap portion 170 is shown having the same width as main body portion 162, it is contemplated that strap portion 170 can be one or more narrow members extending outwardly from main body portion 162 at any location. Optionally, but preferably, one or more tabs 172 are provided to securely attach catheter tube 166 to the stabilizing device 160. Moreover, tab 172 is preferably made of the same self-adherent, non-adhesive material as main body 162 to facilitate attachment and remove of tabs 172.

FIGS. 10–21 show various additional embodiments of the present invention. Each embodiment is of a stabilizing device 200. The device 200 includes a main body 202 having a window 204 to allow passage of IV catheter (not shown). The main body 202 is made from an extensible surgical grade material as describe above. Main body 202 further includes a front portion 206 connected to a rear portion 208 by a pair of side portions 210. At least one of the side portions 210 maybe provided with a slit 212 (shown in phantom) to enable window 204 to be placed around the previously installed catheter. The slit 212, however, is optional with every embodiment of the present invention. A plurality of straps 214 are connected to side portions 210 and extend outwardly away from main body 202. Straps 214 are preferably integral with main body 202 and are made of a same extensible surgical grade material. In every embodiment further described below, the window 204 further includes at least one tab. The tab(s) are also made from the same surgical grade material and are used to secure the catheter tube to the main body 202 of the device 200. The shape and features of the tabs are the distinguishing features of the various embodiments in FIGS. 10–21.

Figure 10:
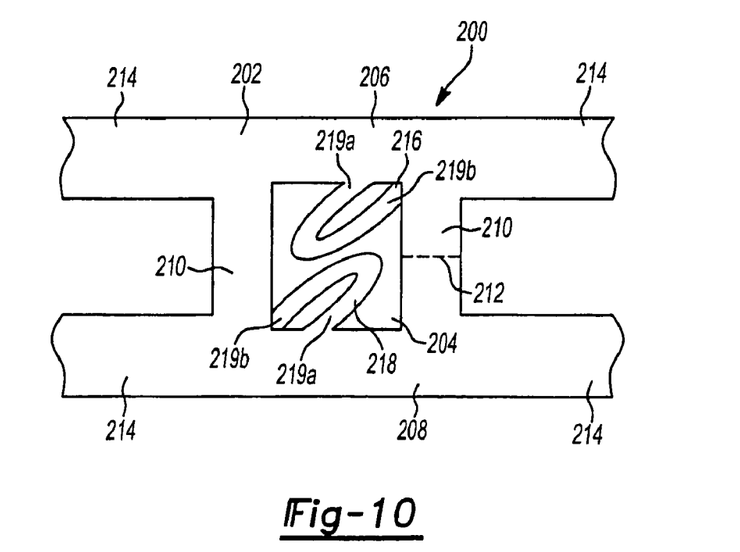
FIG. 10 is a top view of a tenth embodiment of the present invention.

In FIG. 10 the window 204 has an upper tab 216 and a lower tab 218. The upper tab 216 and lower tab 218 are generally U-shaped and are attached to a main body 202 portion of the stabilizing device at one end 219a. The opposite ends 219b of the U-shaped tabs 216, 218 are not attached to the main body 202 and remain free to attach to a catheter tube. In a preferred embodiment, each tab 216, 218 extends from a diametrically opposed corner of the window 204. However, it is understood that ends 219a,b may extend from a side surface of the window 204. The U-shaped design allows increased visibility of the insertion area of the catheter while still providing a technique to secure the tubing to the main body 202 of the stabilizing device 200.

Figure 11:
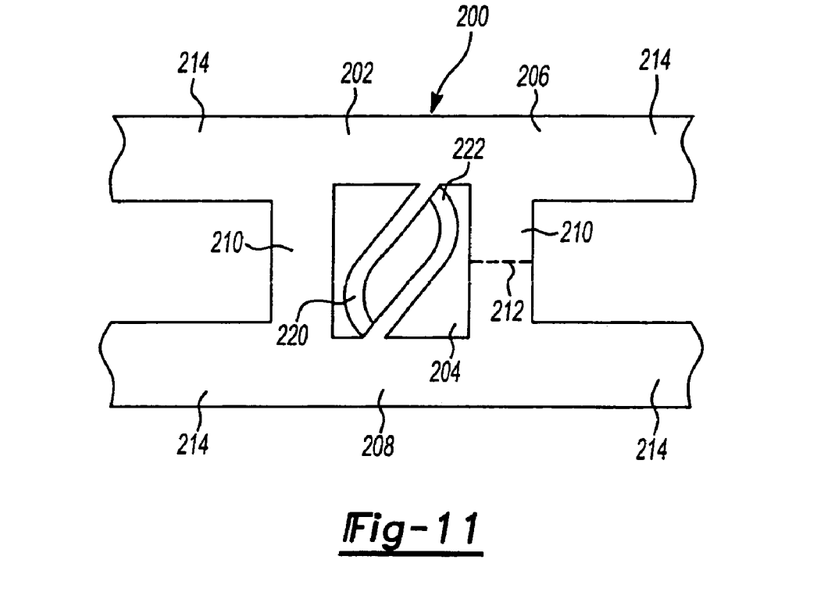
FIG. 11 is a top view of an eleventh embodiment of the present invention.

In FIG. 11 the window 204 has a left tab 220 and a right tab 222 both of a generally curved shaped. The tabs 220, 222 are each attached at one end to the main body 202. The opposite ends remain free but are abutted against the opposite tab 220,222. When the device 200 is not in use the tabs 220,222 lie flat to form a partial figure-8 shape. This configuration of the tabs 220, 222 again increases the visibility of the catheter insertion site area.

Figure 12:
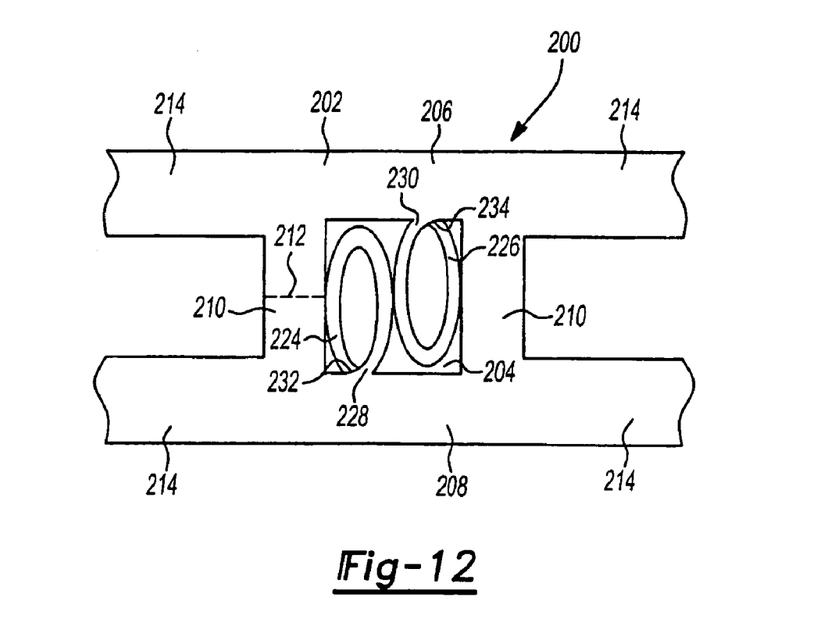
FIG. 12 is a top view of a twelfth embodiment of the present invention.

In FIG. 12 the window 204 has at least one tab 224, 226. In one preferred embodiment, the tabs 224, 226 are loops that lie in parallel. Each tab 224, 226 is integrally attached with the main body 202 at one end 228, 230. The opposite ends 232, 234 remain free and abut against the first attached end 228, 230 of the tabs 224, 226. The looped configuration of the tabs 224, 226 stabilizes the catheter tube while increasing visibility of the catheter insertion site area.

Figure 13:
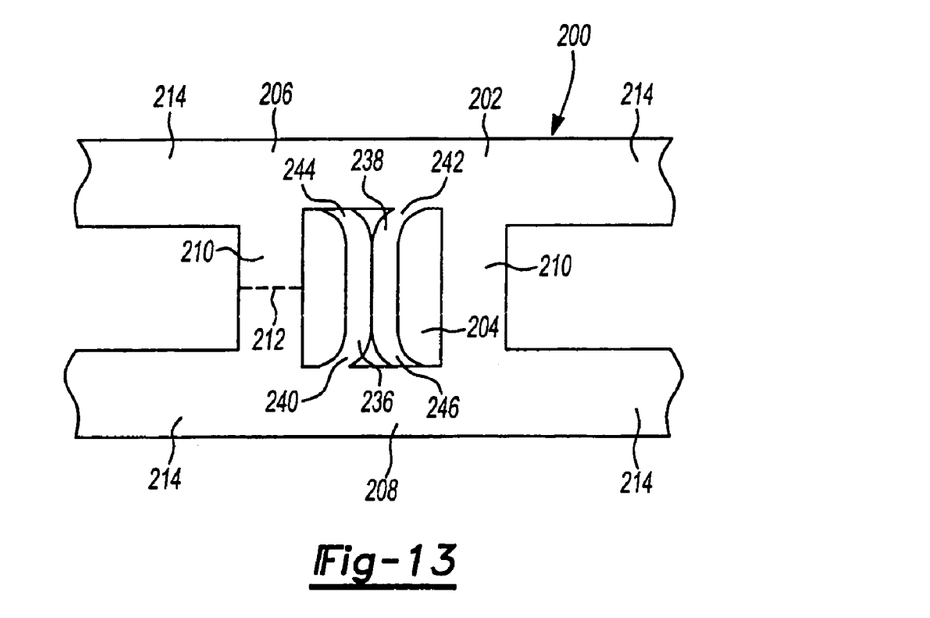
FIG. 13 is a top view of a thirteenth embodiment of the present invention.

In FIG. 13 within the window 216 are a left tab 236 and a right tab 238. The tabs 236, 238 are generally C-shaped and abut against each other in a back-to-back configuration. One end 240, 242 of each tab 236, 238 is integrally attached to the main body 214 while the opposite ends 244, 246 are not attached and abut against the edge of the window 204.

Figure 14:
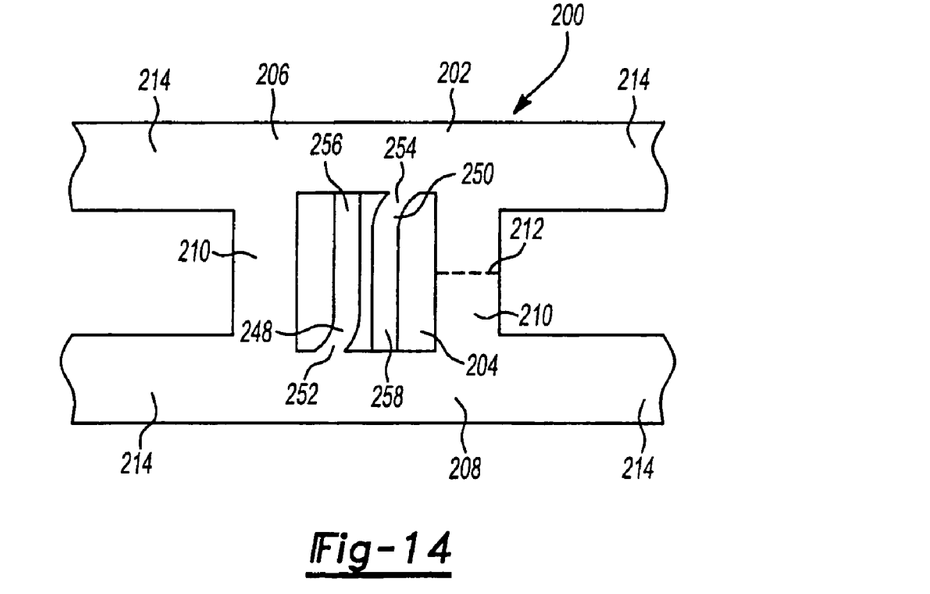
FIG. 14 is a top view of a fourteenth embodiment of the present invention.

In FIG. 14 the window 204 includes a left tab 248 and a right tab 250 of a generally J-shaped configuration. The curved ends 252, 254 of the tabs 248, 250 are attached to the main body 202 while the opposite ends 256, 258 abut the end of the window 204.

Figure 15:
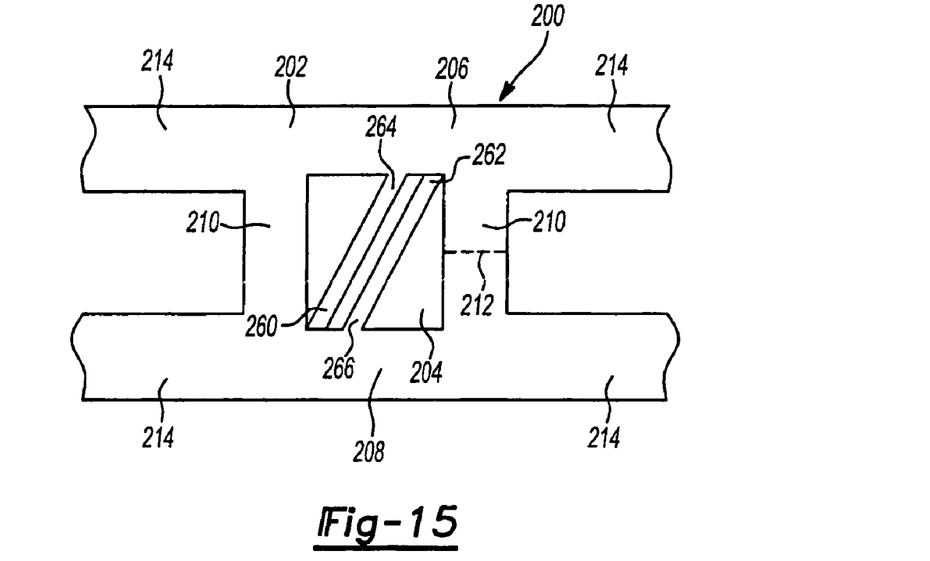
FIG. 15 is a top view of a fifteenth embodiment of the present invention.

In FIG. 15 the window 204 includes two tabs 260, 262. The tabs 260, 262 are generally straight and parallel to each other. Each tab 260, 262 runs diagonally from opposite corners of the window 204. Only one end 264, 266 of each tab 260, 262 is attached to the main body. The opposite end remains free. The attached ends 264, 266 of the tabs 260, 262 are at opposite corners.

Figure 16:
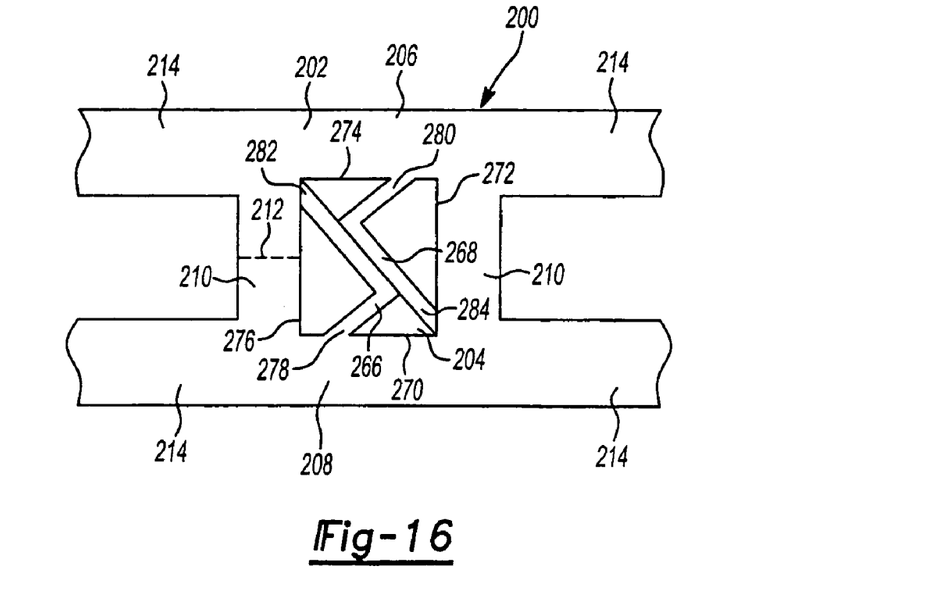
FIG. 16 is a top view of a sixteenth embodiment of the present invention.

FIG. 16 illustrates another embodiment of the present invention of a stabilizer device 200. The window 204 includes a left tab 266 and a right tab 268 of a generally L-shaped configuration. A first end 278 of the left tab 266 is integrally formed with one side 270 of the window 204. A first end 280 of the right tab 268 is integrally formed with another side 274 of the window 204. The sides 270, 274 of the window 204 integrally formed with the tabs 266, 268 are opposite from each other. The free ends 282, 284 of the tabs 266, 268 abut the remaining sides 276, 272 of the window 204.

Figure 17:
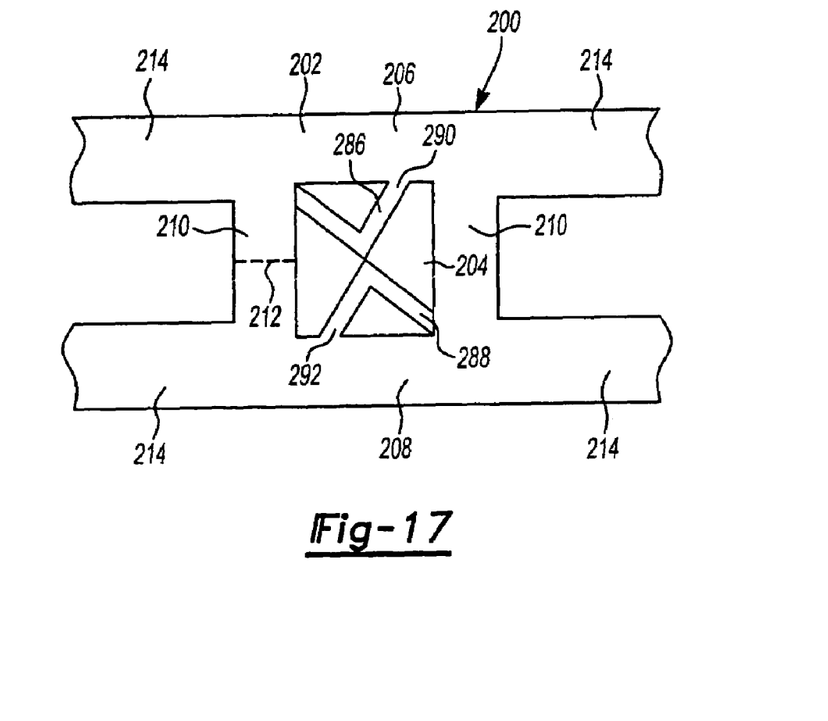
FIG. 17 is a top view of a seventeenth embodiment of the present invention.

In FIG. 17 the window 204 includes an upper tab 286 and a lower tab 288. The tabs 286, 288 are generally V-shaped. One end of each tab 290, 292 is integrally formed with the main body 202 while the opposite end remains free and abuts against the edge of the window 204. The tabs 286, 288 also abut each other at their tips. As with the other embodiments the V-shaped design permits increased visibility of the insertion site area of the catheter while securing the catheter tubing to the device 200.

Figure 18:
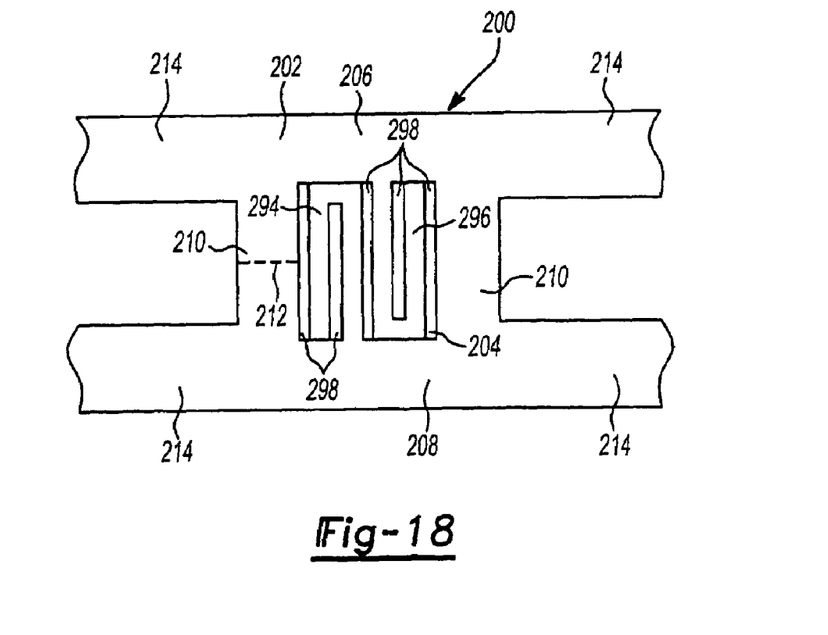
FIG. 18 is a top view of a eighteenth embodiment of the present invention.

FIG. 18 shows yet another embodiment of the present invention of a stabilizing device 200. In the window 204 are a left tab 294 and a right tab 296. The tabs 294, 296 are again of a U-shaped configuration. However, as compared to the tabs 216, 218 in FIG. 10, the tabs 294, 296 of the present embodiment are extremely vertical and have squared corners. The tabs 294, 296 each have an attached end and a free end. Both ends are on the same edge of the window 204. The bottom of the U-shape rests on the opposite edge of the window 204 than the attached or free ends. Additionally, the tabs 294, 296 are parallel and opposite of each other. The attached end of left tab 294 is on an opposite edge of the window 204 than the attached end of the right tab 296. The same is true for the free ends of each tab 294, 296. Tabs 294, 296 of this configuration create a plurality of panes 298 in which to view the insertion site area of the catheter.

Figure 19:
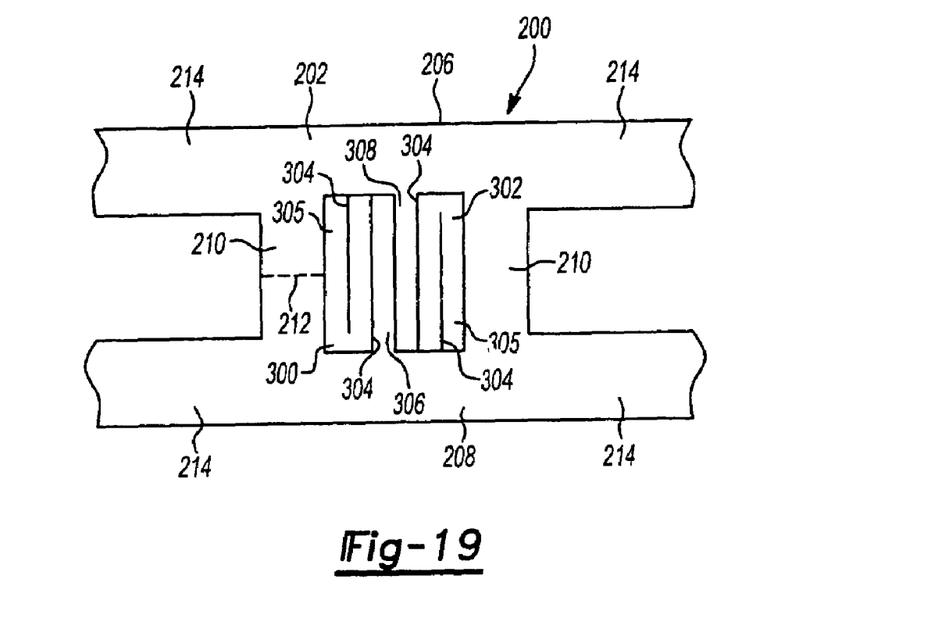
FIG. 19 is a top view of a nineteenth embodiment of the present invention.

FIG. 19 illustrates an alternative embodiment of the present invention. Instead of the window 204 as illustrated in the embodiment described above, the present embodiment includes generally S-shaped tabs 300, 302 formed in the center of the main body 206 by a plurality of slits 304. The S-shaped tabs 300, 302, as shown in the present view, are inverted and abut against each other. One end 306, 308 of each tab is integrally attached to the main body 202 of the device 200. The remaining portion of the tabs 300, 302 are in the s-shaped configuration. When lying in a flat orientation, the s-shaped tabs 300, 302 completely cover the opening to receive the catheter. However, corners may be lifted to view the area distal to the catheter insertion site.

Figure 20:
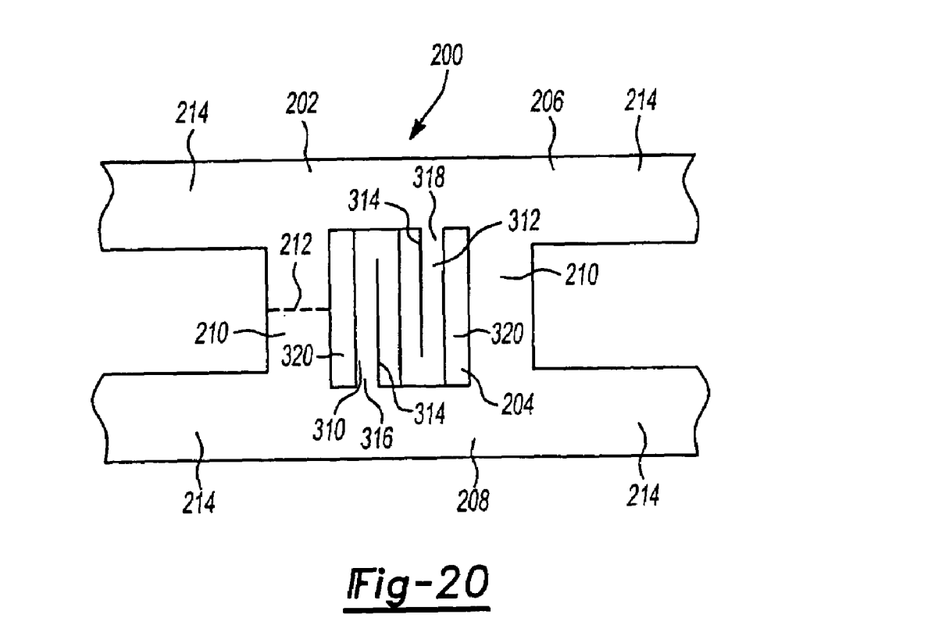
FIG. 20 is a top view of a twentieth embodiment of the present invention.

In FIG. 20 the window 204 includes a left tab 310 and a right tab 312. The tabs 310, 312 are again U-shaped as in FIG. 18 and extremely vertical with squared corners. These tabs 310, 312, however, have only slits 314 to form the u-shape. Again, only one end 316, 318 of each tab 310, 312 is integrally attached to the main body 202 of the device 200. The opposite end of the tabs 310, 312 remain free and abut against the edge of the window 204. The two tabs 310, 312 are positioned adjacent to each other in the window 204 to form viewing panes 320 on each side of the tabs 310, 312. The panes 320 are used to improve visibility of the catheter insertion site area.

Figure 21:
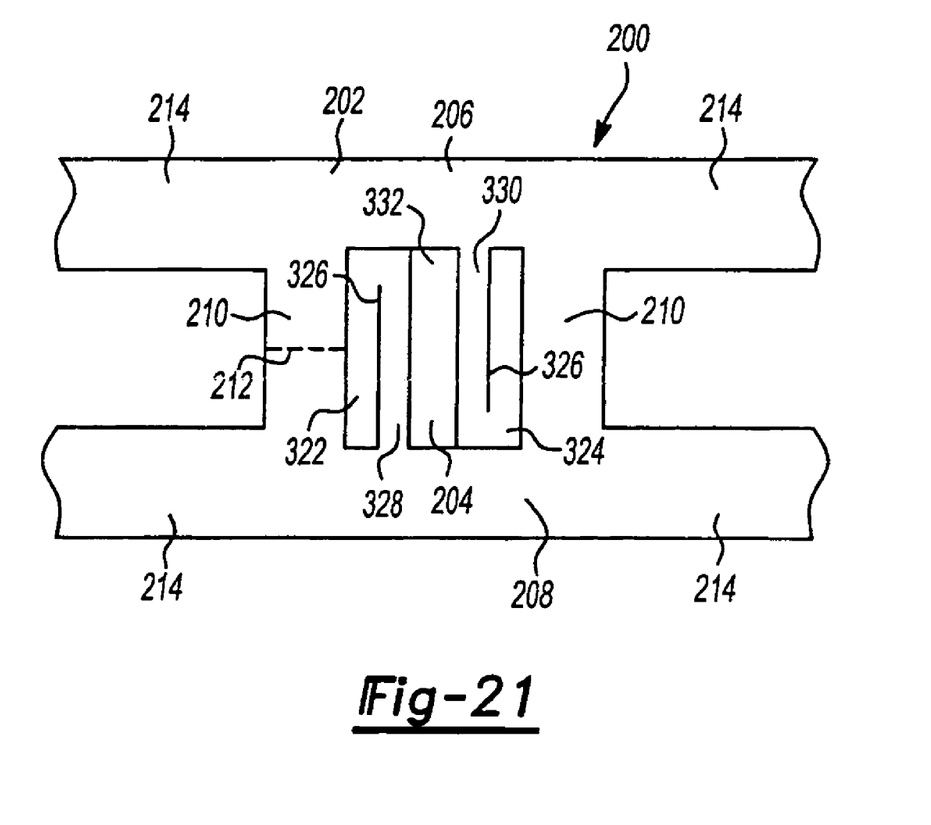
FIG. 21 is a top view of a twenty-first embodiment of the present invention.

The final embodiment in FIG. 21 is very similar to the embodiment in FIG. 20. Again the window 204 includes a left tab 322 and a right tab 324. The tabs 322, 324 are the extremely vertical, squared corner U-shape configuration. The tabs 322, 324 include a slit 326 in the center and have one end 328, 330 integrally attached to the main body 202 of the device 200. The tabs 322, 324, however, are not positioned adjacent to each other but at opposite ends of the window 204. This positioning creates a pane 332 in the center between the tabs 322, 324. Again, this pane 332 increases visibility of the catheter insertion site.

It is contemplated that any of the different window embodiments discussed above can be used with any type of overall stabilizing device. For example, although window 120 in FIG. 4 is illustrated on a stabilizing device having four straps, it is able to be adapted to any of the other stabilizing devices such as in FIGS. 2 or 6.

Preferred embodiments of the present invention have been disclosed. A person of ordinary skill in the art would realize, however, that certain modifications would come within the teachings of this invention. Therefore, the following claims should be studied to determine the true scope and content of the invention.

We claim:

1. A stabilizing device for securing a catheter to a patient's body at a catheter insertion site, the stabilizer device comprising:
   a main body for positioning over the catheter insertion site;
   a window formed in said main body and being of sufficient size for permitting passage of a catheter therethrough;
   at least one attachment member connected to said main body for securely attaching said stabilizing device to a patient;
   at least one tab member connected to an edge of said window for securing said catheter; and
   wherein both said main body and said at least one attachment member are formed from a homogeneous self-adherent material that is extensible;
   wherein the main body and said at least one attachment member is non-adhesive to said patient's body.

2. The stabilizing device of claim 1, wherein said main body includes a front portion connected to a rear portion by a pair of spaced apart side portions.

3. The stabilizing device of claim 2 wherein said main body includes a slit formed in one of said front, rear or side portions and connected to said opening to allow said main body to be positioned around a previously installed catheter without requiring catheter removal.

4. The stabilizing device of claim 1, wherein said main body is generally flexible for adapting to contours of a patient's body near the catheter insertion site.

5. The stabilizing device of claim 1, wherein said main body and said at least one attachment member are formed integrally from a single piece of material.

6. The stabilizing device of claim 1, wherein said at least one attachment member is a single strap extending outwardly from said main body.

7. The stabilizing device of claim 1, wherein said at least one attachment member is a plurality of straps extending outwardly from said main body.

8. The stabilizing device of claim 1, wherein said at least one tab member has a generally curved shape forming a partial figure-8 configuration, wherein one end of said tab member is integral with said edge of said window.

9. The stabilizing device of claim 1, wherein said at least one tab member has a generally U-shaped configuration, wherein one end of said tab member is integral with said edge of said window.

10. The stabilizing device of claim 1, wherein said at least one tab member has a generally C-shaped configuration, wherein one end of said tab member is integral with said edge of said window.

11. The stabilizing device of claim 1, wherein said at least one tab member has a generally J-shaped configuration, wherein one end of said tab member is integral with said edge of said window.

12. The stabilizing device of claim 1, wherein said at least one tab member has a generally L-shaped configuration, wherein one end of said tab member is integral with said edge of said window.

13. The stabilizing device of claim 1, wherein said at least one tab member has a generally V-shaped configuration, wherein one end of said tab member is integral with said edge of said window.

14. The stabilizing device of claim 1, wherein said at least one tab member has a straight tab attached diagonally from opposite corners of the window, wherein one end of said tab member is integral with said edge of said window.

15. The stabilizing device of claim 1, wherein said at least one tab member has a generally S-shaped configuration, wherein one end of said tab member is integral with said edge of said window.

16. The stabilizing device of claim 1, wherein said at least one tab member has a generally oval shape with an end portion that is integral with said edge of said window.

* * * * *